United States Patent [19]
Mackool

[11] Patent Number: 5,830,176
[45] Date of Patent: Nov. 3, 1998

[54] MAINTENANCE OF PRESSURE WITHIN A SURGICAL SITE DURING A SURGICAL PROCEDURE

[76] Inventor: Richard J. Mackool, 31-27 41st. St., Astoria, N.Y. 11103

[21] Appl. No.: 578,833

[22] Filed: Dec. 26, 1995

[51] Int. Cl.⁶ .................................................. A61B 17/20
[52] U.S. Cl. .............................. 604/22; 604/28; 604/31; 604/34; 607/107; 606/169
[58] Field of Search .................... 604/27, 28, 30, 604/31, 49–51, 65–67, 80, 81, 257, 258, 259, 290, 294, 22, 23; 128/645, 675, 676, 748, 751–3; 606/166–171, 169; 607/107

[56] References Cited

U.S. PATENT DOCUMENTS

| | | | |
|---|---|---|---|
| 3,693,613 | 9/1972 | Kelman | 606/107 |
| 4,168,707 | 9/1979 | Douvas et al. | 604/118 |
| 4,496,342 | 1/1985 | Banko | 604/27 |
| 4,548,205 | 10/1985 | Armeniades et al. | 128/748 |
| 4,573,974 | 3/1986 | Ruschke | 604/81 |
| 4,650,462 | 3/1987 | DeSatnick | 604/30 |
| 4,650,642 | 3/1987 | DeSatnick et al. | 604/30 |
| 4,722,350 | 2/1988 | Armeniades et al. | 128/748 |
| 4,750,643 | 6/1988 | Wortrich | 604/80 |
| 4,832,685 | 5/1989 | Haines | 604/30 |
| 4,841,984 | 6/1989 | Armeniades et al. | 128/748 |
| 5,084,009 | 1/1992 | Mackool | 604/22 |
| 5,167,620 | 12/1992 | Ureche et al. | 604/28 |
| 5,354,265 | 10/1994 | Mackool | 606/128 |
| 5,387,201 | 2/1995 | Fowler | 604/290 |
| 5,403,276 | 4/1995 | Schechter et al. | 604/22 |
| 5,520,652 | 5/1996 | Peterson | 604/30 |
| 5,554,155 | 9/1996 | Awh et al. | 604/294 |
| 5,562,612 | 10/1996 | Fox | 604/27 |
| 5,591,127 | 1/1997 | Barwick, Jr. et al. | 604/66 |
| 5,643,203 | 7/1997 | Beiser et al. | 604/27 |

Primary Examiner—Mark Bockelman
Attorney, Agent, or Firm—Cobrin Gittes & Samuel

[57] ABSTRACT

Varying flow rate and/or the fluid pressure head through a surgical instrument by selecting which of a plurality of fluid lines will supply fluid through the infusion line of the instrument. The fluid lines connect with supply ports of a common connector that has a common discharge port in fluid connection with the infusion line. The fluid lines are each in fluid connection with either a common fluid source, fluid sources at different elevations, or fluid sources at different or the same pressures. Flow control may be based on opening and closing of valves in the flow lines or operating and stopping operation of pumps or vacuum devices. A controller may determine which flow control to implement based on sensing of pressure changes in the eye or on known capacities of the pumps or vacuum devices. The sensing may be effected with a pressure transducer within the eye, but spaced from the infusion and aspiration lines of the surgical instrument.

24 Claims, 5 Drawing Sheets

MAINTENANCE OF PRESSURE WITHIN A SURGICAL SITE DURING A SURGICAL PROCEDURE

REFERENCE TO COPENDING PATENT APPLICATIONS

U.S. patent application Ser. No. 08/400,802, filed Mar. 8, 1995, and entitled IMPROVED METHOD AND APPARATUS FOR REDUCING FRICTION AND HEAT GENERATION BY AN ULTRASONIC DEVICE DURING SURGERY now U.S. Pat. No. 5,505,693; U.S. patent application Ser. No. 08/419,817, filed Apr. 11, 1995, and entitled APPARATUS FOR CONTROLLING FLUID FLOW THROUGH A SURGICAL INSTRUMENT AND THE TEMPERATURE OF AN ULTRASONIC INSTRUMENT now U.S. Pat. No. 5,569,188; and U.S. patent application Ser. No. 08/514,555, filed Aug. 14, 1995 and entitled SUPPORT FOR FLUID INFUSION TUBE FOR USE DURING EYE SURGERY now U.S. Pat. No. 5,685,841.

BACKGROUND OF THE INVENTION

1. Field of the Invention

The present invention relates to an apparatus and method for maintaining pressure within a surgical site during a surgical procedure by varying flow through a surgical instrument to prevent pressure surges. This may be done by switching between fluid sources at different elevations or between fluid sources at different pressures, combining flows from such fluid sources, or making such alterations in the fluid sources based on the setting of the vacuum pressure or flow rate of a pump mechanism. A pressure measuring device may be used, such a pressure transducer located within the body organ and spaced from the irrigation and aspiration tip of the surgical instrument.

2. Discussion of Related Art

During the procedure of cataract removal known as phacoemulsification, a console with a controller is employed to set the pumping rate and/or vacuum level through an aspiration tube from a surgical instrument. Setting the pumping rate and/or vacuum level at greater levels results in a faster rate of fluid flow through the eye, and consequently a lowering of the pressure within the eye. A fluid surge condition may also arise during the performance of the procedure; the fluid surge condition arises when the fluid flow rate is higher than that which was intentionally set at the console that controls pumping rate and/or vacuum pressure.

While the existence of a fluid surge may account for the rate of fluid removal from the eye to become variable, I have observed that fluid may be removed from the eye at a variable rate even in the absence of such a fluid surge. For instance, such variable rate of fluid removal may occur intentionally where the aspiration flow rate and/or vacuum level is set in such a manner as to intentionally produce a greater flow of fluid from the eye.

On the other hand, such variable rate fluid removal may occur unintentionally due to partial or complete obstruction of the aspiration tube at any point by tissue fragments being aspirated through the tube. The removal of such tissue would result in a changing flow rate even if it were not abrupt enough to result in a fluid surge.

A result from such variable flow rate is variable intraocular pressure. I have performed literally thousands of cataract eye operations, and, based on my experience, have found that the procedure of phacoemulsification of the eye is more efficiently and safely performed if the intraocular pressure is maintained above 20 mm Hg. However, I have performed studies on human cadaver eyes which indicate that it is common for the pressure to fall well below 20 mm Hg and even as low as 0 to 5 mm Hg during periods of high flow rate.

When the pressure within the eye is maintained at this level of 20 mm Hg. or higher, the volume of the eye chamber (within which the phacoemulsification procedure is performed) remains more constant and delicate structures such as the posterior capsule and iris tend to remain at a greater distance from the surgical instruments being employed than would otherwise be the case if the pressure level within the eye were at a lower level.

Surgical instruments, such as ultrasonic and non-ultrasonic aspirating instruments, are used to remove tissue fragments. Such instruments are connected to a fluid source, which supplies the necessary irrigation of the eye through an irrigation conduit within the surgical instrument. Attempts at maintaining intraocular pressure within the eye have been limited to varying the height of an infusion source, or pressurizing the infusion source. These methods cannot be used to rapidly adjust inflow into the eye as required by rapid changes in outflow rate. Intraocular pressure therefore fluctuates widely during all currently performed cataract operations.

The following U.S. patents are incorporated by reference, each of which names myself, Richard Mackool, as inventor, and which disclose, among other things, a surgical instrument suitable for use with the present invention: U.S. Pat. No. 5,084,009, issued Jan. 28, 1992 and entitled FLUID INFUSION SLEEVE FOR USE DURING EYE SURGERY, U.S. Pat. No. 5,354,265, issued Oct. 11, 1994 and entitled FLUID INFUSION SLEEVE, and U.S. Pat. No. 5,286,256, issued Dec. 15, 1994 and entitled FLUID INFUSION SLEEVE. Also, incorporated by reference are the contents of U.S. patent application Ser. No. 08/400,802, filed Mar. 8, 1995, and entitled IMPROVED METHOD AND APPARATUS FOR REDUCING FRICTION AND HEAT GENERATION BY AN ULTRASONIC DEVICE DURING SURGERY now U.S. Pat. No. 5,505,693 and U.S. patent application Ser. No. 08/419,817, filed Apr. 11, 1995 now U.S. Pat. No. 5,569,188, and entitled APPARATUS FOR CONTROLLING FLUID FLOW THROUGH A SURGICAL INSTRUMENT AND THE TEMPERATURE OF AN ULTRASONIC INSTRUMENT, and U.S. patent application Ser. No. 08/514,555, filed Aug. 14, 1995 and entitled SUPPORT FOR FLUID INFUSION TUBE FOR USE DURING EYE SURGERY now U.S. Pat. No. 5,685,841.

In phacoemulsification, eye surgeons typically rely on a single source of fluid for infusion. It is, of course, common for eye surgeons to change the elevation of such single fluid infusion source relative to the patient eye level during the course of the phacoemulsification procedure for purposes of changing the pressure in the eye or the rate of removal of tissue fragments from the eye.

Such a technique for maintaining intraocular pressure is obviously cumbersome in that the bottle height (for a gravity fed fluid system) would have to be changed many times during the operation and cannot be done rapidly in response to the sudden changes in flow rate that occur during surgery, and therefore cannot prevent the changes in intraocular pressure which result. It would be desirable to avoid relying on a single source of fluid to maintain intraocular pressure, and to avoid the need to manually vary the bottle height to respond to sudden changes in pressure that arise during surgery.

In addition, it is conventional practice to locate a pressure transducer along the aspiration conduit within the surgical instrument to sense pressure within the eye. However, it is well known that pressure transducers that are located at a point distant from the eye such as along an aspiration conduit frequently indicate a pressure which is lower than that which is actually within the eye. In other words, there is a pressure gradient between the eye and the aspiration conduit within the surgical instrument, which is the reason why fluid flows from the eye through the aspiration conduit.

This pressure gradient does not remain constant, however, because of the frequent occurrence of partial or complete obstructions within the aspiration conduit in the region between the eye and the transducer. It would therefore be desirable to obtain a pressure measurement that actually reflects the pressure within the eye regardless of such pressure gradient, and previous devices have been described for this purpose. For instance, see U.S. Pat. No. 4,548,205 and U.S. Pat. No. 4,722,350.

SUMMARY OF THE INVENTION

One aspect of the invention relates to varying flow through a surgical instrument. Based either on sensing pressure within a human organ such as an eye or on known pump capacities, fluid flow through an irrigation or infusion tube of the surgical instrument is regulated accordingly to avoid an unacceptable level of deflation of the human organ. Fluid flow may be from any number of fluid sources whose flow lines feed into a common infusion tube that leads to the infusion conduit. The flow lines have flow control devices, such as valves or pumps, which are operative to permit or cease fluid flow through any given flow line. Alternatively, multiple infusion conduits or tubes may be inserted into the body organ to deliver fluid.

BRIEF DESCRIPTION OF THE DRAWING

For a better understanding of the present invention, reference is made to the following description and accompanying drawings, while the scope of the invention is set forth in the appended claims.

DESCRIPTION OF THE PREFERRED EMBODIMENT

Figure 1:
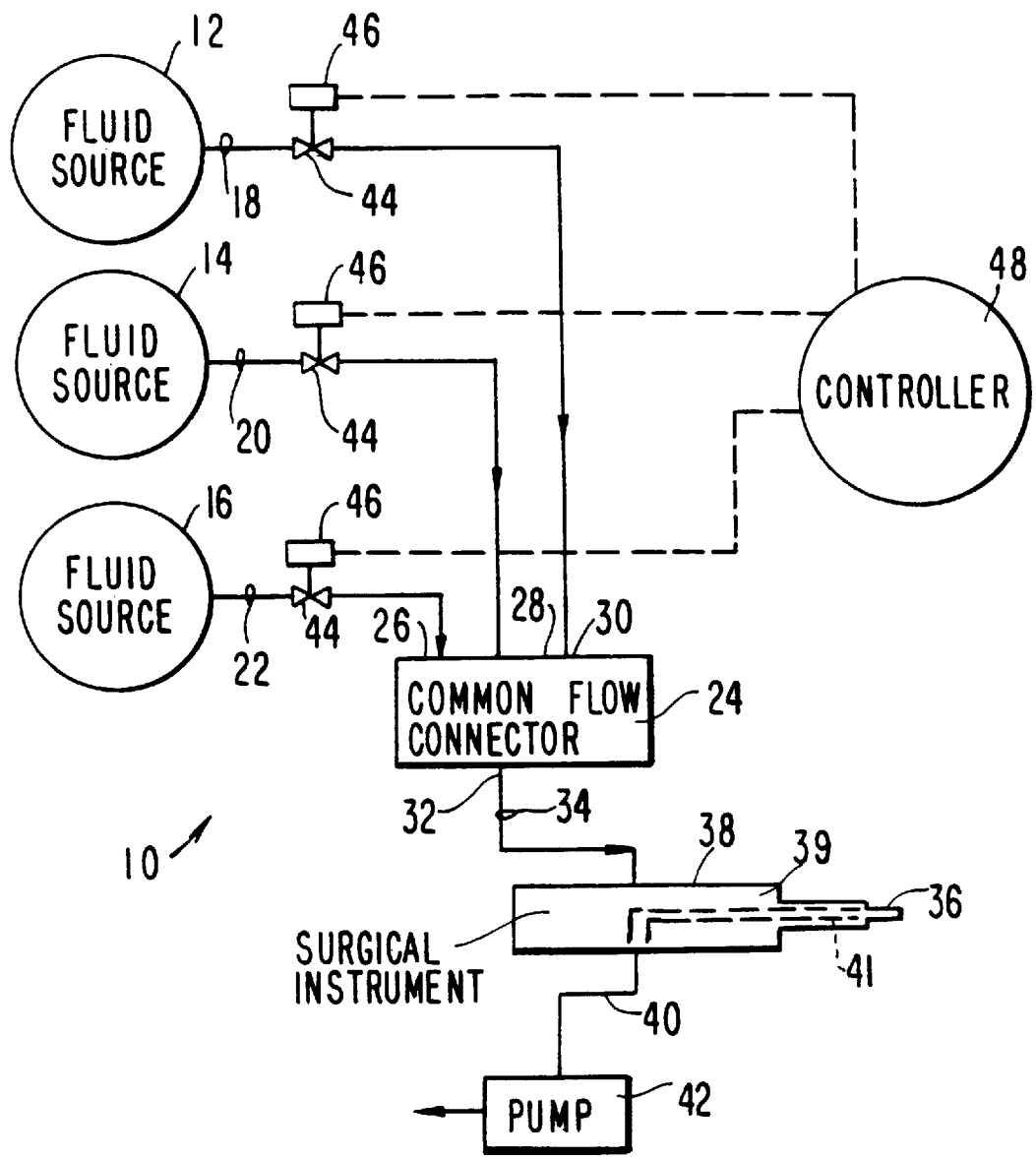
FIG. 1 is a schematic representation of a fluid varying apparatus in accordance with a first embodiment of the invention.

FIG. 1 shows a fluid varying apparatus 10 having a plurality of fluid sources 12, 14, 16 at different elevations, a plurality of flow lines 18, 20, 22 each extending from a respective one of the fluid sources to convey fluid to a common flow connector 24, which has supply ports 26, 28, 30 to which is sealingly connected the flow lines 18, 20, 22 in a corresponding manner. The common flow connector 24 has a discharge port 32 to which is connected an infusion tube 34 that connects with an infusion conduit 39 (shown only in outline in FIG. 1) in a surgical instrument 38. However, the infusion conduit terminates at the tip 36.

The instrument 38 also has an aspiration conduit 41 (shown in outline in FIG. 1) through whose tip at 36 is drawn fluid and tissue fragments from the body organ, such as an eye. Such aspiration arises preferably from operation of a pump 42 providing suction through the aspiration tube 40. The fluid sources may be open or closed to atmosphere. Typically, the infusion conduit radially surrounds the aspiration conduit. A vibratory instrument (not shown) may be used to break the tissue of the body organ into fragments for removal.

Each of the flow lines contains a respective flow control device 44, such as a valve, that is operative with associated drivers 46 between an open condition and a closed condition. A controller 48 is provided to send instructions to the drivers 46 to actuate and de-actuate as warranted based on a determination made by the controller 48. Such a determination is based upon sensed or known information, such as by measuring pressure of the eye and determining whether a pressure level or rate of pressure declination within the eye is acceptable or some combination of these parameters is acceptable. Otherwise, if the parameter aspiration flow rate and/or vacuum pressure is set for the pump and this information is received by the controller, the controller may make a determination as to which, or combination, of the flow lines should supply fluid through the connector and satisfy this set parameter and send instructions for carrying this out. For instance, for very high settings, the controller 48 may signal the flow control device 44 or valve on the flow line to open that leads to the flow source (or bottle) at the highest elevation.

Once the controller 48 determines that a greater flow rate and/or pressure head through the infusion tube is needed, it may control the valves in the flow lines 18, 20, 22 so that either additional fluid flow is added to that currently present or a fresh supply of fluid is tapped instead.

As an alternative embodiment, the fluid sources 12, 14 and 16 may be at different pressures, whether or not at different elevations as well. To attain such pressure difference, the fluid sources are closed to atmosphere and are under their own respective pressure that is different from that of the others.

Figure 2:
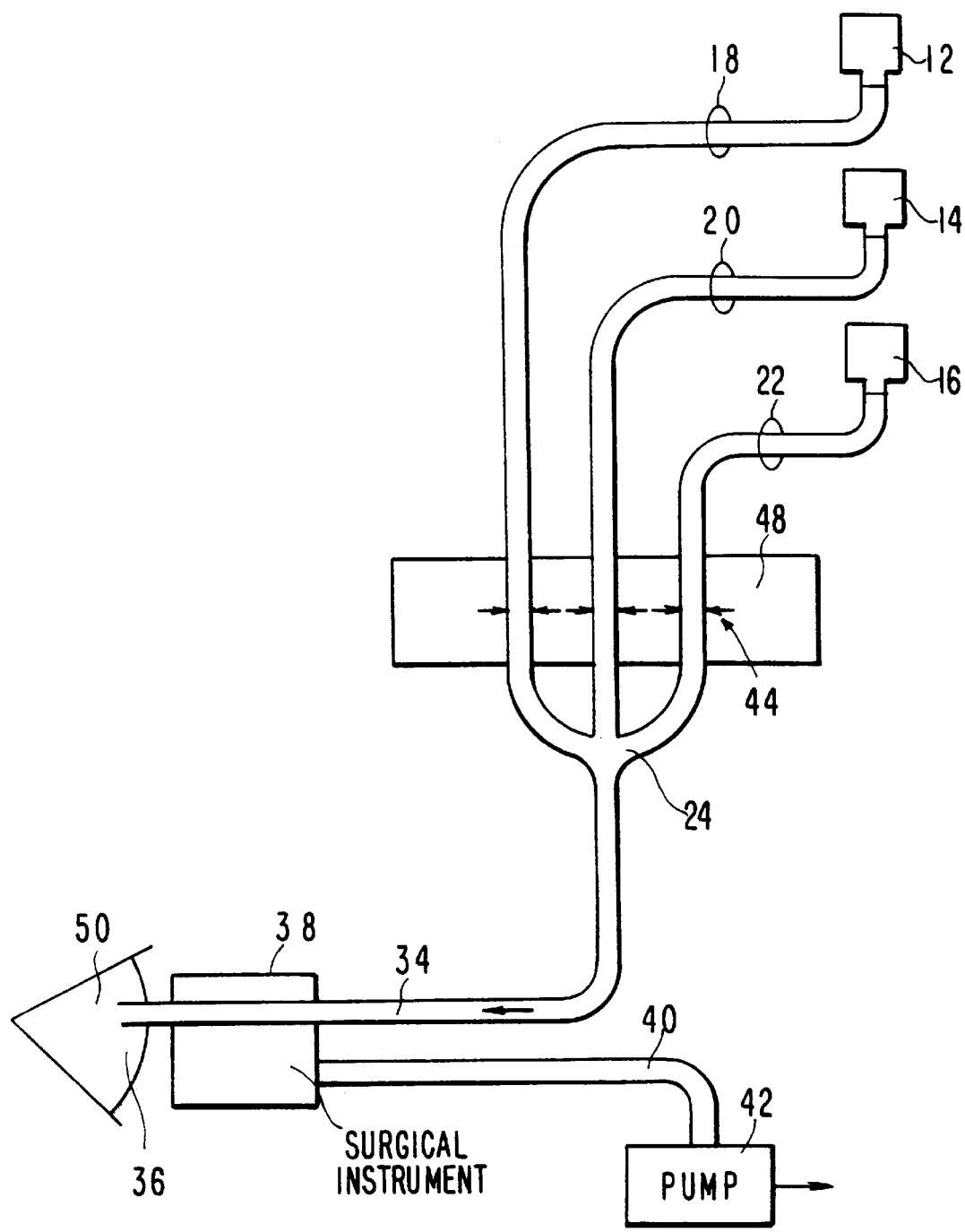
FIG. 2 is a schematic representation of the fluid varying apparatus in accordance with a second embodiment.

FIG. 2 shows a schematic representation of another embodiment operating along the same principles as that of FIG. 1, but showing the eye 50. The flow control device 44 in the case may simply be actuated by a driver to squeeze the flow lines 18, 20, 22 to close them or release under spring tension to open them. They need not be motorized gate valves, although the effect is the same. The particular construction of the surgical instrument 38 is not crucial to the invention; for instance, the infusion and aspiration conduits may arranged side by side or the aspiration conduit may be radially surrounded by the infusion conduit. The fluid sources 12, 14, 16 may be in the form of bottles at different elevations.

Figure 3:
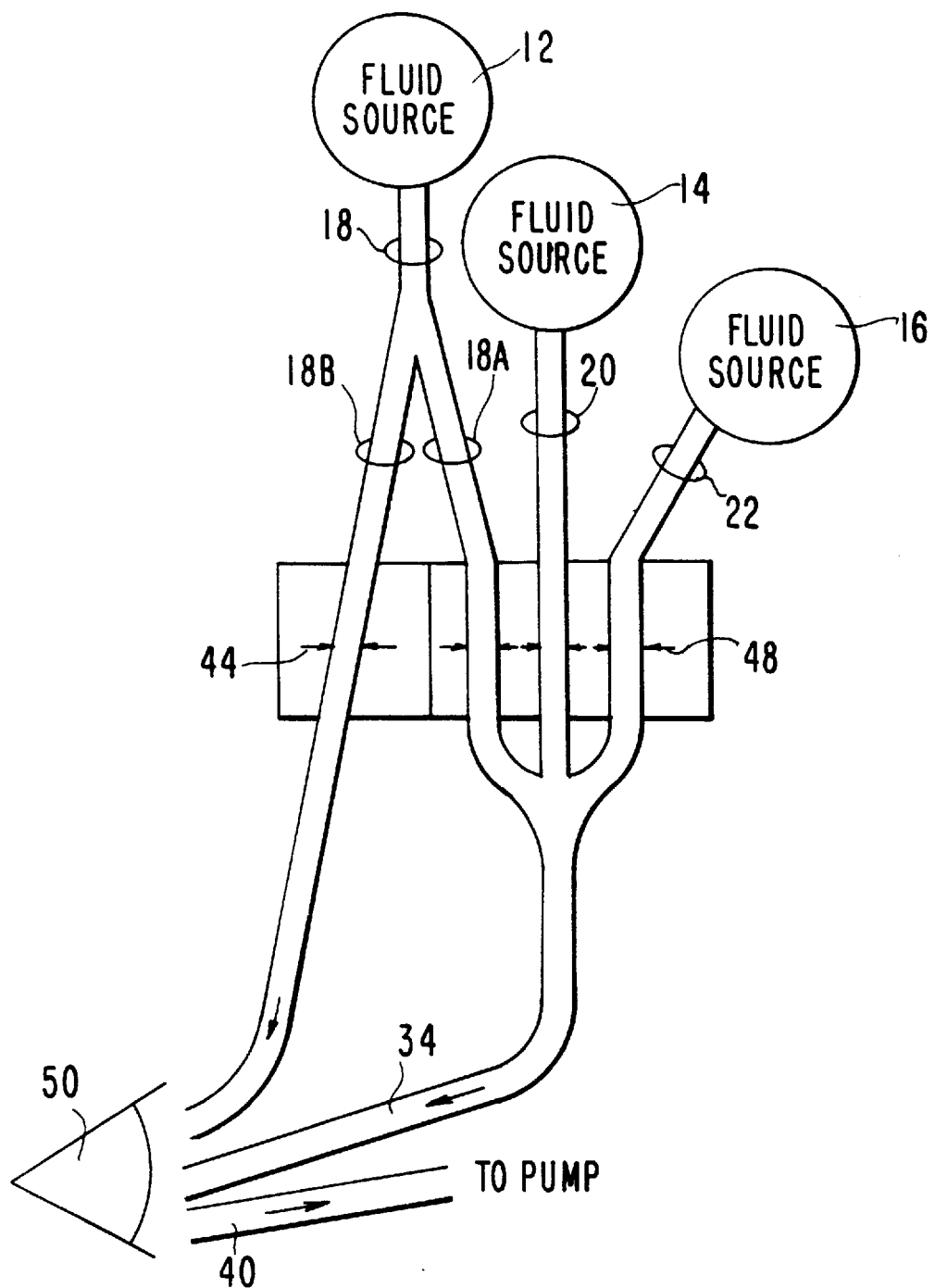
FIG. 3 is a schematic representation of the fluid varying apparatus in accordance with a third embodiment.

FIG. 3 shows another embodiment in which one or more of the flow lines 18, 20, 22 are bifurcated between the fluid source 12, 14, 16 and flow control device 44 so that the now bifurcated lines (e.g., 18A, 18B) each provide fluid infusion to the eye independently of each other. For instance, bifurcated line 18B may provide infusion through line 34, but bifurcated line 18A provides its own infusion. Such bifurcation need not increase the intraocular pressure beyond that afforded by the typical system that provides for a single infusion conduit, but it does provide greater potential infusion flow due to the greater area available for infusion when two infusion tubes (or conduits) discharge fluid separately into the eye. Flow line 18 may, in such a circumstance, be of greater diameter than that of lines 20 or 22. Flow lines 18A and 18B could also have diameters which vary from those of lines 20 or 22.

The controller 48 may be programmed with information of the availability of two separate infusion sources that may deliver fluid to the eye 50 (e.g., via lines 18B and 34) and take that into account when determining fluid flow rate and controlling the flow control devices 44.

Figure 4:
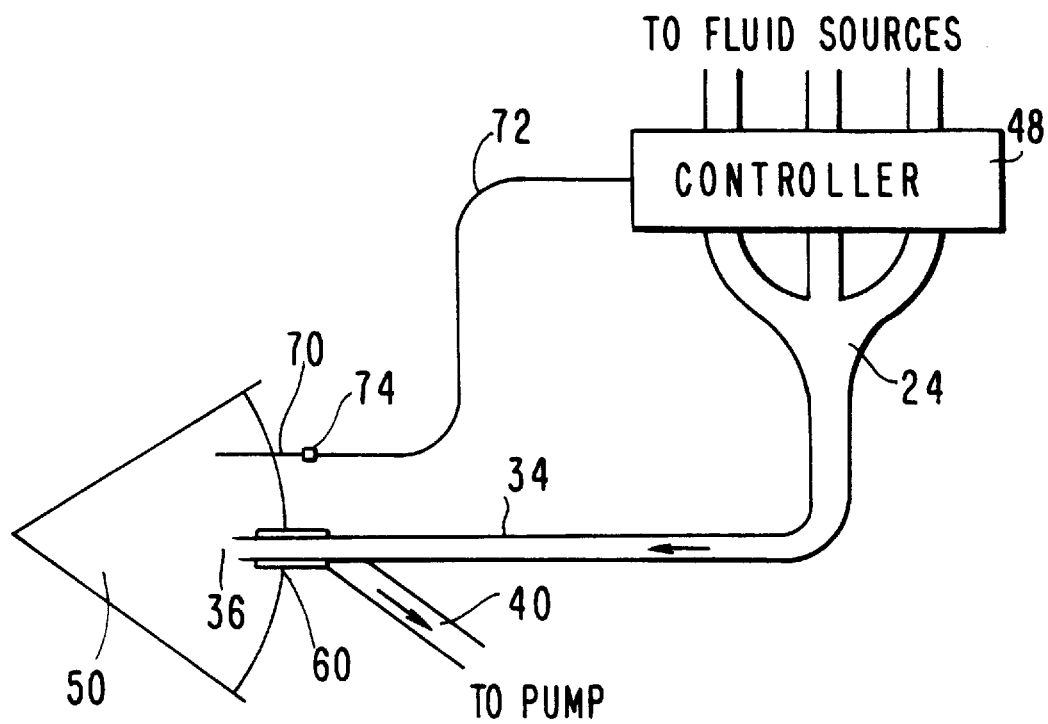
FIG. 4 is a schematic representation of a pressure transducer arranged within the eye in accordance with a fourth embodiment.

FIG. 4 shows a pressure transducer 70 that may be used in conjunction with any of the other embodiments of FIGS. 1–3. While the pressure transducer 70 is shown here within the eye 50 but spaced from the tip 36 and the incision 60, for purposes of measuring pressure, the pressure transducer 70 could be arranged within one of the tubes.

Nevertheless, the preferred embodiment is that the pressure transducer 70 be spaced from the tubes to ensure accuracy of pressure readings at all times. If it were within the tube, there is a risk that the pressure measured would be affected by pressure effects attributed to any tissue fragments that cause partial blockage of the aspiration tube. For instance, if the pressure transducer were arranged along the aspiration tube, but the tissue fragments became temporarily lodged between the pressure transducer and the open end of the aspiration tube, the pressure sensed by the pressure transducer might thereby fail to accurately reflect the true pressure within the eye.

In accordance with the preferred embodiment, a small pressure transducer 70 is placed within the eye at any location within the anterior or posterior chamber. Its placement is completely independent of the infusion and aspiration tubes. Indeed, the transducer 70 may be constructed to have a pointed end so that it could be inserted in a needle-like fashion through the peripheral cornea or the transducer may be incorporated into an instrument, such as a straight metallic spatula, that is separate from the surgical instrument containing the infusion and aspiration tubes. In this manner, the transducer could measure the intraocular pressure directly. Both possibilities are intended to be represented in FIG. 4 as shown.

Such a pressure transducer 70 would be constructed of materials that are sterilizable; it may be either reusable or disposable for single use only.

The transducer 70, upon sensing pressure, transmits appropriate signals through a signal line such as a fiberoptic cable 72, which may be loosely tied together with the surgical instrument 38 for organizational purposes of concentrating tubing leaving the eye for the controller 48, although it need not be. The controller may be a microprocessor.

Suitable pressure transducers are those commercialized by INNERSPACE Corp., 1923 S.E. Main St., Irvine, Calif. 92714, which developed a 0.8 mm diameter fiberoptic sensor that transmits monochromatic light along an optical fiber to a pressure sensitive template that reflects light. The resulting phase changes are used by the transducer to compare with a reference light beam and thereby analyze pressure changes.

Other suitable pressure transducers are those commercialized by FIBEROPTIC SENSOR TECHNOLOGIES, 501 Avis Drive, Ann Arbor, Mich. 48108, which developed a fiberoptic sensor that recognizes changes in the intensity of light which is reflected from a pressure sensitive diaphragm.

The small pressure transducers would be held in place either by the surgeon, in the case where they are incorporated into or otherwise connected to a spatula or other type of instrument, or retained by the snugness of the incision through which they are inserted.

If desired, a protuberant portion 74 may be provided that surrounds the fiberoptic cable at a desired distance from the pressure transducer to prevent inadvertent migration of the pressure transducer into the eye.

There is no maximum pressure value that should be avoided during surgical operation of the eye. Practically speaking, it would be nearly impossible to exceed an intraocular pressure of 100 mm Hg.; there is no point in doing so. The invention should respond either to a pressure drop to a specific limit or to a rate of pressure drop that exceeds an acceptable declination in the rate of pressure drop or to a formulation that takes into account both of these parameters. For example, it may be desirable that an extremely rapid drop from 80 to 40 mm Hg. would trigger the opening of a valve, but a slow drop from 50 to 40 mm Hg. would not. The rates which are considered "rapid" or "slow" as to trigger the opening or maintaining closure of the valve could be calculated by extrapolating the amount of time required at that rate of declination to reach 10 mm Hg. and comparing with the time in which additional fluid and/or pressure is expected to have an effect to raise the pressure upon commencement of instructions to open the flow control device or valve.

Figure 5:
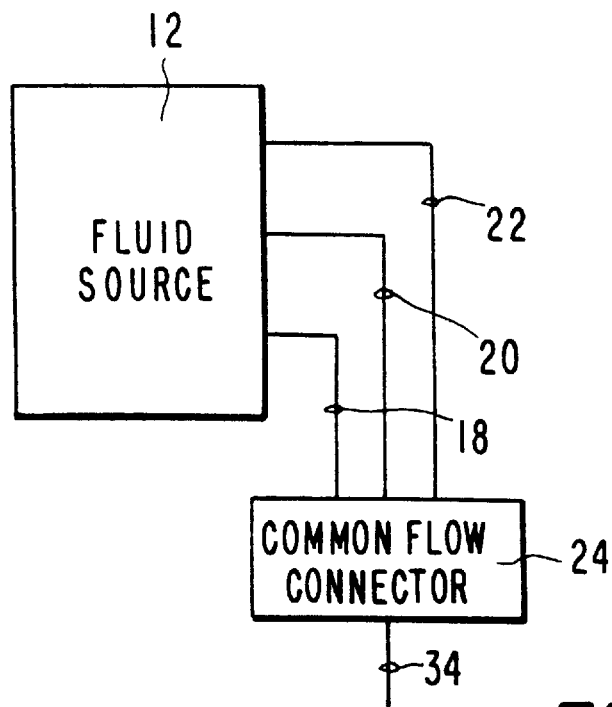
FIG. 5 is a schematic representation of the fluid varying apparatus in accordance with a fifth embodiment.

In FIG. 5, the flow lines 18, 20, 22 come off a common fluid source 12, but each is taken off at a different elevation. In that sense, the arrangement is comparable to that of FIGS. 1 or 2 in that fluid from different elevations may be drawn upon for infusion. Where the fluid source 12 is a bottle containing fluid, the level should be monitored to avoid dropping beneath the location of the inlet to the uppermost flow line, i.e., line 22.

Figure 6:
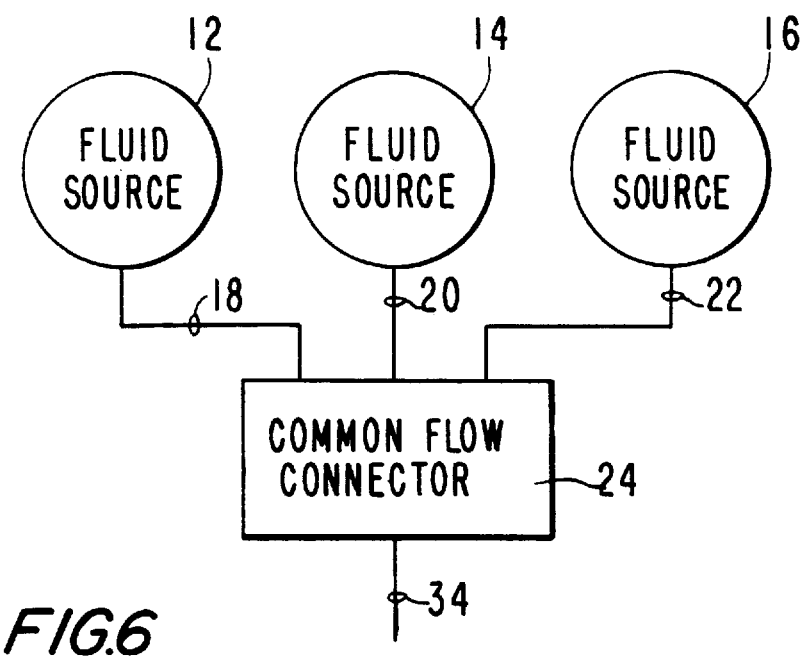
FIG. 6 is a schematic representation of the fluid varying apparatus in accordance with a sixth embodiment.

FIG. 6 shows another embodiment that differs from the others in that all the fluid sources are at the same elevation. Ideally, the fluid pressure in each differs from each other so that the controller (not indicated in this view) may select the appropriate source from which fluid will be drawn to provide needed pressure.

If the pressure in each is the same, the arrangement in FIG. 6 is still useful in that it allows for an increase in the volume of flow through the infusion tube 34 by combining the flows from one or more of the lines 18, 20, 22 together. Of course, infusion tube 34 must be of a larger diameter than the flow lines 18, 20, 22 to accommodate the larger volume if two or more flow lines are permitted to feed their fluid into the infusion tube 34. In this sense, it may be used in the same manner as the embodiment of FIG. 3.

For purposes of brevity, only the fluid source, flow lines, common flow connector and the infusion tube are shown in FIGS. 5 and 6. All the components shown in the other embodiments of FIGS. 1–4, however, may be used here as well, i.e., flow control devices or valves, the surgical instrument, the aspiration tube, the pump, the controller, the pressure transducer, etc.

The application has used the terms irrigation tube and irrigation conduit; aspiration tube and aspiration conduit. Where a surgical instrument 38 is being used, typically it contains conduits, which in turn are connected to respective tubes for infusion or aspiration. If the surgical instrument is separate from the infusion and aspiration tubes, however, it will not have such conduits. Thus, when reference is made to bringing the infusion or aspiration tip 36 to the eye, it could refer either to that of the surgical instrument 38 or independent lines (e.g., FIG. 3). For purposes of covering both situations, the term aspiration line will be used to refer to either via the aspiration tube directly or via the aspiration conduit, and the term infusion line will be used to refer to either via the infusion tube directly or via the infusion conduit.

The term surgical instrument, as used hereafter, covers any type of medical instrument used in connection with surgery that makes provision for infusion of fluid to the surgical site and aspiration of tissue fragments from the surgical site. It includes a phacoemulsification instrument, but is not necessarily limited to that type.

While the foregoing description and drawings represent the preferred embodiments of the present invention, it will be understood that various changes and modifications may be made without departing from the spirit and scope of the present invention.

What is claimed is:

1. An apparatus for maintaining pressure, comprising:

a surgical instrument that is a phacoemulsification instrument operable to cut tissue into tissue fragments;

an infusion line extending through the surgical instrument to convey fluid to flow therethrough to a surgical site neighboring an incision;

an aspiration line extending through the surgical instrument through which flows fluid from the surgical site to remove the tissue fragments from the surgical site;

a connector having a plurality of supply ports and having a discharge port connected to the infusion line;

a plurality of flow lines each connected to a respective one of the supply ports;

a fluid supply connected to each of the plurality of the flow lines, said fluid supply, said plurality of flow lines, said connector, said irrigation line and said aspiration line being arranged relative to each other such in response to fluid flowing through said connector and said infusion line to the surgical site, fluid flows together with any tissue fragments from the surgical site through said aspiration line regardless of which of the flow lines fluid flows through from said fluid supply to said connector;

a pressure sensor that senses changes in pressure at one of the surgical site and the aspiration line;

fluid control equipment responsive to sensed changes in the pressure as sensed by said sensor to vary flow through the flow lines.

2. An apparatus as in claim 1, wherein the fluid supply includes a plurality of fluid sources each adapted to be arranged at different elevations and each connected to a respective one of the flow lines.

3. An apparatus as in claim 1, wherein the fluid supply includes a plurality of fluid sources each having different pressures and each connected to a respective one of the flow lines.

4. An apparatus as in claim 1, wherein the fluid supply is a reservoir of fluid and is common to each of the flow lines.

5. An apparatus as in claim 1, wherein said fluid supply includes a plurality of pressurized fluid reservoirs each connected to a respective one of the flow lines. controller being programmed to direct that at most one of the valves be open at any one time.

6. An apparatus as in claim 1, wherein said fluid control equipment includes valves each in a respective one of the flow lines and drivers that open and close respective ones of the valves, the pressure sensor sensing pressure indicative of a condition that requires an increase in flow rate through the discharge port beyond flow capacity of an opened one of the valves alone, a controller that selectively directs the drivers to open and close the valves in the flow lines, the controller being programmed to direct that a plurality of the valves be open at the same time in response to the sensed changes in pressure that are indicative of an occurrence of the condition that requires an increase in flow rate through the discharge port beyond flow capacity of an opened one of the valves alone.

7. An apparatus as in claim 6, wherein the controller is adapted to make a determination as to whether the sensed pressure changes are indicative of any one of a pressure level drop below an acceptable level and a rate of pressure drop decline exceeding an acceptable rate of decline and, if so, providing direction to increase the flow rate through the discharge port.

8. An apparatus as in claim 1, wherein the fluid control equipment is in the flow lines, the pressure sensor being arranged to sense changes in pressure that warrant an increase in flow through the discharge port, the controller being responsive to the sensed changes in pressure to determine whether the increase in flow through the discharge port is warranted and, if so, sending control signals to the fluid control equipment, which responds to increase the flow through the discharge port.

9. An apparatus as in claim 1, wherein the flow control equipment includes valves each in a respective one of the flow lines and drivers that open and close respective ones of the valves, the controller being arranged to selectively direct the drivers to open and close the valves, the controller being programmed to direct that at most one of the valves be open at any one time.

10. An apparatus as in claim 1, wherein said flow control equipment includes valves in the flow lines, the valves being operable to open, the pressure sensor being arrnaged to sense changes in pressure at the surgical site, the controller making a determination as to whether an increase in the flow rate is warranted based on the sensed pressure by the sensor and, if so, directing drivers to selectively open and close valves to increase the flow rate through the discharge port.

11. An apparatus as in claim 10, wherein the controller makes a determination as to which of the valves should open to provide the increase in the flow rate through the discharge port based on available flow rates through each of the flow lines.

12. An apparatus as in claim 1, wherein the fluid control equipment includes a conveyor of fluid adapted to force the conveyance of fluid through the surgical instrument; and the controller being arranged to instruct which of the flow lines is to supply fluid through the connector based on settings of the conveyor of fluid.

13. An apparatus as in claim 1, wherein said pressure sensor is responsive to changes in pressure at the surgical site neighboring the incisiion; the sensor being spaced from and arranged exteriorly of each of the infusion and aspiration lines; said flow control equipment including a flow regulating device that varies a rate of flow through at least one of the lines in response to the changes in pressure as sensed by the sensor.

14. An apparatus as in claim 13, wherein the flow regulating device, based on the changes in the pressure as sensed by the sensor, determines whether a level of pressure at the surgical site drops below an acceptable level and, if so, causes the rate of fluid flow to increase through the infusion line to bring the level of the pressure closer to the acceptable level.

15. An apparatus as in claim 13, wherein the flow regulating device, based on the changes in the pressure as sensed by the sensor, determines whether a rate of pressure drop at the surgical site drops below an acceptable rate for a level of the pressure at the surgical site and, if so, causes the rate of fluid flow to increase through the infusion line to bring the level of the rate of pressure drop closer to the acceptable level.

16. An apparatus as in claim 13, further comprising a fiberoptic cable connected with the sensor.

17. A method of varying flow rate through a surgical instrument, comprising the steps of:

supplying fluid to flow from a fluid supply through at least one of a plurality of flow lines, each of the flow lines connecting a fluid supply with a respective one of a plurality of supply ports of a connector;

conveying the fluid from any of the flow lines to respective ones of the supply ports and then through the connector to discharge through a discharge port of the connector and thereafter enter an infusion line of a surgical instrument;

irrigating a surgical site with the conveyed fluid in the infusion line by dispensing the conveyed fluid from the surgical instrument;

aspirating the dispensed fluid together with tissue fragments from the surgical site through an aspiration line of the surgical instrument regardless of which of the flow lines fluid was conveyed during the step of conveying, the surgical instrument being a phacoemulsification instrument operable to cut the tissue into the tissue fragments;

sensing pressure chances at one of the surgical site and the aspiration line:

automatically varying flow through the flow lines in response to the sensed pressure changes.

18. A method as in claim 17, wherein the step of sensing detects changes in pressure at the surgical site neighboring the incision that is exteriorly spaced from the aspiration line and the infusion line; and the step of varying flow is in response to the changes in pressure as sensed from the step of sensing.

19. A method as in claim 18, further comprising the step of determining, based on the changes in the pressure as sensed the sensor, whether a level of pressure at the surgical site drops below an acceptable level and, if so, causing the rate of fluid flow to increase through the infusion line to bring the level of the pressure closer to the acceptable level.

20. A method as in claim 18, further comprising the step of determining, based on the changes in the pressure as sensed the sensor, whether a rate of pressure drop at the surgical site drops below an acceptable rate for a level of the pressure at the surgical site and, if so, causing the rate of fluid flow to increase through the infusion line to bring the level of the rate of pressure drop closer to the acceptable level.

21. A method as in claim 18, further comprising the step of inserting a sensor through an incision in the eye, the sensor effecting the step of sensing.

22. A method as in claim 21, wherein the step of inserting is effected by inserting a spatula that incorporates the sensor.

23. A method as in claim 21, wherein the step of inserting is effected by inserting a pointed end of the sensor.

24. A method as in claim 18, further comprising the step of ensuring that a pressure within the surgical site remains under a medically safe pressure level above which may cause some deflation in a vicinity of the surgical site.

* * * * *

UNITED STATES PATENT AND TRADEMARK OFFICE
CERTIFICATE OF CORRECTION

PATENT NO. : 5,830,176
DATED : November 3, 1998
INVENTOR(S) : RICHARD J. MACKOOL It is certified that error appears in the above-identified patent and that said Letters Patent is hereby corrected as shown below:

Claim 1, column 7, line 38, after "such" insert -- that --.

Signed and Sealed this

Thirteenth Day of April, 1999

*Attest:*

Q. TODD DICKINSON

*Attesting Officer*  *Acting Commissioner of Patents and Trademarks*